United States Patent
Zisapel et al.

(10) Patent No.: US 6,780,884 B2
(45) Date of Patent: Aug. 24, 2004

(54) DERIVATING OF TRYPTAMINE AND ANALOGOUS COMPOUNDS AND PHARMACEUTICAL FORMULATIONS CONTAINING THEM

(75) Inventors: Nava Zisapel, Tel Aviv (IL); Moshe Laudon, Kfar Saba (IL)

(73) Assignee: Neurim Pharmaceuticals (1991) Ltd., Tel Aviv (IL)

(*) Notice: Subject to any disclaimer, the term of this patent is extended or adjusted under 35 U.S.C. 154(b) by 0 days.

(21) Appl. No.: 10/381,976
(22) PCT Filed: Sep. 25, 2001
(86) PCT No.: PCT/IL01/00898
§ 371 (c)(1),
(2), (4) Date: Aug. 28, 2003
(87) PCT Pub. No.: WO02/28347
PCT Pub. Date: Apr. 11, 2002

(65) Prior Publication Data
US 2004/0029950 A1 Feb. 12, 2004

(30) Foreign Application Priority Data
Oct. 3, 2000 (IL) .................................. 138825

(51) Int. Cl.[7] ..................... A61K 31/405; C07D 209/04
(52) U.S. Cl. ....................... 514/415; 548/490
(58) Field of Search ........................ 514/415; 548/490

(56) References Cited

U.S. PATENT DOCUMENTS 4,880,826 A    11/1989    Zisapel et al.

OTHER PUBLICATIONS

Keglevic et al., Indole Compounds. 3-(2-mercaptoethyl)indoles and bis-[3-(2-thioethyl)indoles], sulfur analogs of tryptophol, 5-hydroxytryptophol, and other benzyl-substituted tryptophols. *Croat. Chem. Acta.* 1968, pp. 7–14, vol. 40, No. 1.

Edmundson et al., "Binding of 2,4-dinitrophenyl compounds and other small molecules to a crystalline λ-type Bence-Jones dimer," *Biochemistry*, Aug. 27, 1974, pp. 3816–3827, vol. 13, No. 18.

*Primary Examiner*—Taofiq Solola
(74) *Attorney, Agent, or Firm*—Rothwell, Figg, Ernst & Manbeck

(57) ABSTRACT

This invention relates to novel substituted tryptamines and related derivatives, as well as pharmaceutical compositions formulated therefrom. These compounds, compositions and their salts can be used in the manufacture of medicaments for interacting with the melatoninergic system. These compounds and conditions can be used for treating several types of medical conditions, such as central nervous system and psychiatric disorders (sleep disorders, epilepsy and other convulsive disorders, anxiety, neurodegenerative diseases), chronobiological-based disorders (jet lag, delayed sleep syndrome, shift-work, seasonal affective disorder), neoplastic conditions, and conditions associated with senescence.

10 Claims, No Drawings

DERIVATING OF TRYPTAMINE AND ANALOGOUS COMPOUNDS AND PHARMACEUTICAL FORMULATIONS CONTAINING THEM

This Appl. is a 371 of PCT/IL01/00898 file Sep. 25, 2001.

FIELD OF THE INVENTION

The present invention relates to new compounds which are derivatives of tryptamine and their analogs, pharmaceutical formulations containing them, and use of the compounds in the manufacture of medicaments for treating various diseases.

BACKGROUND OF THE INVENTION

Melatonin is the principal hormone secreted by the pineal gland in all vertebrates. In all mammals studied to date, including humans, a nocturnal rise in the production of melatonin by the pineal gland is evident; melatonin production by the body is acutely suppressed by light. Melatonin is involved in the coordination of photoperiod dependent and physiological processes. The ability of the animals or humans to respond to the melatonin signal may depend upon melatonin receptors. Melatonin acts on the CNS to affect neural mechanisms through receptors located in the brain. Additionally, a number of studies indicate the existence of direct effects of melatonin in peripheral organs via peripheral melatonin receptors. Melatonin receptors are present in the heart, lungs, prostate gland, gonads, white blood cells, retina, pituitary, thyroid, kidney, gut and blood vessels. Retention patterns of radioactive-melatonin injected to rats demonstrate melatonin accumulation in the brain, pituitary, lung, heart, gonads and accessory sex organs (Withyachumnamkul et al., Life Sci 12:1757–65, 1986).

The synthesis and secretion of melatonin exhibit a circadian rhythm that changes with the seasons and with age, e.g., pubescence and senescence. There is very strong evidence that melatonin is important for the regulation of a variety of neural and endocrine functions, especially those that exhibit circadian and circannual rhythmicity.

Melatonin has been implicated in many human disorders. Some are known to be linked to chronobiological abnormalities. Melatonin has been administered to re-synchronize circadian rhythms that are out of phase with the local photoperiodical cycle. For example, sleep/wake disorders with rapid crossing of time zones jet lag), or in delayed sleep phase syndrome (DSPS) patients, changes in work shifts, or those experienced by blind people can be treated with melatonin or melatonin analogs (see U.S. Pat. Nos. 4,600, 723 and 4,666,086 of Short et al. and U.S. Pat. No. 5,242, 941 of Lewy et al.).

However, it appears that melatonin also has direct sedative/hypnotic properties in normal human subjects (e.g., Waldhauser et al., Psychopharmacology, 100: 222–226, 1990; Vollrath et al., Bioscience 29:327–329, 1981: Dollins et al., Proc. Natl. Acad. Sci, 99:1824–1828, 1994, U.S. Pat. No. 5,403,851 of D'Orlando et al). Three melatonin receptor subtypes have been identified so far mt-1, MT-2 and Me11c (Barrett et al., Biol. Signals Recept., 1999, 8: 6–14). MT-2 is localized mainly in the central nervous system and mt-1, localized in the CNS as well as in peripheral organs such as kidney and the urogenital tract (Dubocovich et al., IUPHAR media, London, UK, 187–93, 1998). The presently known subtypes are not sufficient to evaluate the large variety of melatonin effects and additional receptor subtypes await discovery.

Melatonin has been demonstrated in a number of rodent experimental paradigms to have both anxiolytic (Golus and King, Pharmacol. Biochem. Behav., 41:405–408, 1992, Naranjo-Rodriguez et al., Soc. Neurosci. Abst. 18:1167, 1992; Golombek et al., Eur. J. Pharmacol, 237:231–236, 1993) and antiseizure activity (Brallowsky, Electroencephalo. clin. Neurophysiol. 41:314–319, 1976: Farielloet al., Neurology 27:567–570, 1977, Rudeen et al., Epilepsia 21:149–154, 1980; Sugden, J. Pharmacol Exp. Ther. 227:587–591, 1983; Golombek et al., Eur. J. Pharmacol 210:253–258, 1992).

Melatonin is effective in the treatment of cluster headache and migraine (Claustrat et al., Headache, 29:241–4, 1989). Melatonin may play a role in other psychiatric conditions, particularly depression, but also mania and schizophrenia (see Dobocovich "Antidepressant Agents", U.S. Pat. No. 5,093,352; Miles and Philbrick, Biol. Psychiatry 23:405–425, 1988: Sandyk and Kay, Schizophr. Bull. 16:653–662, 1990). In some instance, psychiatric disorders may have underlying chronobiological etiologies (e.g. seasonal effective disorder) and are definite candidates for melatonin therapy.

Melatonin is involved in the regulation of circadian and circannual changes in body temperature. Administration of exogenous melatonin to humans lowers core body temperature (Strassman et al., J. Appl. Physiol, 71:2178–2182, 1991; Cagnacci et al., J. Clin. Endocrinol. Merab. 75:447–452, 1992). Melatonin may also possess analgesic properties (Sugden, J. Pharmacol. Exp. Ther. 227:587–591, 1983). Therefore, melatonin-like compounds may be useful as an alternative to non-steroidal anti-inflammatory, anti-pyretic drugs, such as aspirin, acetaminophen and ibuprofen.

It is known that melatonin levels decrease with advancing age (Sack et al., J. Pineal Res. 4:379–388, 1986; Waldhauser et al., J. Clin. Endocrinol. Metab., 66:648–652, 1988; Van Coavorden et al., Am. J. Physiol. 260:E651–661, 1991) which may contribute to some disorders, Neurodegenerative diseases often associated with aging, such as Alzheimer's and Parkinson's diseases, may be treated with melatoninergic compounds (Maurizi, Med. Hypotheses 31:233–242, 1990; Sandyk, Int. J. Neurosci. 50:37–53, 1990; Skene et al., Brain Rev. 528:170–174, 1990).

Sleep disorders in the elderly have been shown to respond to melatonin treatment (Garfinkel et al., Lancet, 346:541–543, 1995, U.S. Pat. No. 5,498,423 of Zisapel). Soporific effects of melatonin (0.3–240 mg) have been reported in humans following intravenous, intranasal and oral administration. Apart from its soporific effects, exogenous melatonin may affect sleep via its phase-resetting action on the biological clock. Melatonin administration advanced sleep in delayed sleep syndrome patients, and synchronized sleep to the day-night cycles in blind subjects. The efficacy of melatonin (0.3–5 mg/os) for treatment of insomnia has been demonstrated in studies performed mainly with elderly patients, patients treated with atenolol and chronic heart patients, most of which patients have low or distorted melatonin rhythms. In some of these studies, formulations which release melatonin throughout the night were used, in order to circumvent fast clearance of the hormone and to mimic its endogenous profile (Nutrition, 1998, 14: 1–2; The Aging Male, 1998, 1: 1–8). Melatonin, 3 mg, given to patients with sleep disorders and dementia for 21 days, significantly augmented sleep quality and decreased the number of wakening episodes, while agitated behavior at night (sundowning) decreased significantly (Biol. Signals Recept. 1999, 8(1–2): 126–31).

We have recently found that melatonin treatment may be beneficial not only for improving sleep quality, but may also lead to an improvement in the general state of diabetic patients, as indicated by the decrease in HbA1c levels after long-term treatment.

Daily melatonin supplementation to male Sprague-Dawley rats, starting at middle age (10 months) and continuing into old age (22 months) via the drinking water at a dosage of 4 μg/ml, restored the age-related elevated levels of relative (% of body weight) retroperitoneal and epididymal fat, as well as plasma insulin and leptin levels to youthful (4 month) levels (Rasmussen et al., Endocrinology, 1999, 140 (2): 1009–12).

Even osteoporosis may have a melatoninergic component (Sandyk et al., Int. J. Neurosci. 62:215–225, 1992). In fact, melatonin has been suggested to be an anti-aging, anti-stress hormone (Armstrong and Redman, Med. Hypotheses 34:300–309, 1991; Reiter, Bioassays, 14:169–175, 1992). This may be due to its action as a free radical scavenger (Pooggeler et al., J. Pineal Res. 14:151–168, 1993) or its interaction with the immune system (Maestroni and Conti, J. Neuroimmun. 28:167–176 1990; Fraschini et al., Acta. Oncol. 29:775–776 1990, Guerrero and Reiter, Endocr. Res. 18:91–113, 1992). Melatonin may protect from ischemic stroke (Cho et al., Brain Research 755:335–338, 1997), decrease cell-death in Alzheimer's disease (Pappola et al., J Neurosci 17:1683–90, 1997) and lower the risk of SIDS in young infants with low endogenous melatonin levels (Israel Patents Nos. 115861/2 and U.S Pat. No. 5,500,225 of Laudon et al).

Related to the above, are the findings that melatonin has oncostatic properties in a variety of cancers, the most studied being its effect on estrogen receptor positive breast cancers (Blasak and Hill, J. Neural. Transm. Suppl. 21:433–449, 1986; Gonzalez et al. Melanoma. Res.1:237–243, 1991; Lissoni et al. Eur. J. Cancer 29A:185–189, 1993; Shellard et al. Br. J. Cancer 60:288–290, 1989; Philo and Berkowitz, J. Urol. 139:1099–1102, 1988; see U.S. Pat. No. 5,196,435 of Clemens et al. and U.S. Pat. No. 5,272,141 of Fraschini et al.). It is also possible that melatonin has antiproliferative effects on noncancerous cells as well and may be of use to treat benign tumors and proliferative diseases such as BPH (U.S. Pat. No. 5,750,557 and European Patent No. EP 0565296B of Zisapel) and Psoriasis.

A major portion of research on melatonin has been devoted to studying is effects on reproduction, particularly in seasonally breeding species (such as hamsters and sheep), in which melatonin is known to regulate fertility and puberty, hibernation, and coat color. These effects have obvious significance for animal husbandry use. Reproductive endocrine uses in humans for melatonin include: contraceptive and fertility agents, treatment for precocious puberty, treatment for premenstrual syndrome and hyperprolactinemia (Pevre et al., J. Clin. Endocrinol. Metab. 47:1383–1386, 1978; Purry et al., Am. J. Psychiatry 144:762–766, 1987: Waldhauser et al., Clin. Endocrinol. Metab. 73:793–796, 1991; Bispink et al., Pineal Res. 8:97–106, 1990; Cagnacci et al., J. Clin. Endocrinol. Metab. 73:210–220, 1991; Voordouw et al., J. Clin. Endocrinol. Metab. 74:107–108, 1992; see U.S. Pat. Nos. 4,855,305 and 4,945,103 of Cohen et al., and U.S. Pat. No. 5,272,141 of Fraschini et al.). It is likely that melatonin compounds may also be useful in other endocrine conditions, particularly those involving growth hormone (Cramer et al., Arzeneim-Forsch, 26:1076–1078, 1976; Wright et al., Clin. Endocrinol. 24:375–382, 1986; Paccotti et al., Chronobiologica 15:279–288, 1988; Valcavi et al., Clin. Endocrinol. 39:139–199, 1993). Melatonin may serve to reduce prostate enlargement (see above-cited U.S. and EP patents of Zisapel) Orally administered melatonin to castrated juvenile rats inhibited the androgen-dependent growth of the ventral prostate and the seminal vesicles. (Gilad et al., J. of Urol. 159:1069–73, 1998). Recently, we have demonstrated high affinity melatonin receptors in the human benign prostate epithelial cells, which may affect cell growth and viability (Endocrinology, 137:1412–17, 1996).

In addition to the pineal gland, the eye also synthesizes melatonin. Recently melatonin has been implicated in the control of intraocular pressure and may be of use in glaucoma (Samples et al., Curr, Eye, Res. 7:649–653, 1988; Rhode et al., Ophthalmic. Res. 25:10–15, 1993).

The kidney also expresses melatonin receptors and melatonin has been shown to affect vasopressin and urine excretion (Song et al., FASEB J 11:93–100, 1997, Yasin et al., Brain Res. Bull 39:1–5, 1997).

It is clear that there exists a broad range of therapeutic uses for melatonin. Accordingly it is of continuing interest to identify novel compounds that interact with melatoninergic system as potential therapeutic agents. These compounds may offer longer duration, selective localization and greater efficacy to those of melatonin.

Novel compounds related to melatonin, but with pharmacological or pharmacokinetic profiles different from melatonin, are likely to be important new pharmaceuticals, For examples, see U.S. Pat. No. 5,403,851 which discloses the use of substituted tryptamines, phenylalkylamines and related compounds, in order to treat number of pharmaceutical indications including sleep disorders, endocrine indications, immune-system disorders etc. PCT Patent Application No. WO 87/00432 describes compositions, for treating or preventing psoriasis, which contain melatonin or related compounds. European Patent Application No. 0330625A2 discloses the production of melatonin and analogs thereof, for various therapeutic purposes, including the administration of melatonin in combination with an azidothymidine for the treatment of AIDS. Melatonin analogs based on the bioisosteric properties naphthalenic ring and the indole ring has been disclosed in J. Med. Chem. 1992. 35:1484–1485, EP 662471 A2 950712 of Depreux et al., WO 9529173 A1 951102 of Ladlow et al., U.S. Pat. No. 5,151, 446 of Horn et al., U.S. Pat. No. 5,194,614 of Adrieux et al. and U.S. Pat. No. 5,276,051 of Lesieur et al.

Inhibition by melatonin of dopamine release from specific brain areas has been demonstrated in vitro in rats (Zisapel et al., *Brain Res* 1982; 246(1):161–3; *Brain Res* 1982;246(1):161–3) sheep and hamsters (Malpaux et al. *Reprod Nutr Dev* 1999;39(3):355–66). In addition, melatonin was able to reduce excitability of nigrostriatal neurons (Escames etal *Neuroreport* 1996;7(2):597–600) and increase the affinity of D2 dopamine receptors in the rat striatum (Hamdi *Life Sci* 1998;63:2115–20). It may therefore treat disorders associated with increased dopamine release or dopamine supersensitivity, e.g. for tardive—dyskinesia, or cocaine addiction.

Melatonin antagonist are also of potential therapeutic use. A reduction in nigrostriatal dopaminergic activity as that caused by melatonin could lead to worsening of parkinsonian side effects and akathisia, as is indeed supported by findings in animal models of Parkinson disease (Willis and Armstrong *Brain Res Brain Res Rev* 1998; 27(3):177–242). Melatonin antagonists may thus be helpful to prevent the effects of endogenous melatonin in Parkinson's disease. Melatonin antagonists may also be helpful in preventing fatigue and sleepiness of shift workers caused by the increase in endogenous melatonin at night; in blind persons that are not synchronized with the environmental light dark cycle, in delayed sleep phase syndrome patients who secrete melatonin during daytime and in jet lag.

There is evidence suggesting both melatonin agonists and antagonists would be of potential therapeutic use for a variety of maladies and conditions. The present invention addresses the need for more therapeutically selective compounds than melatonin.

The compounds N-(2,4-dinitrophenyl)-5-methoxytryptamine ("ML-23") and N-(2,4-dinitrophenyl)-2-iodo-5-methoxytryptamine, are known to have antagonistic effects on melatonin (Zisapel et al 1989, U.S. Pat. No. 4,880,826, Laudon et al, J Endocrinol. 1988; 116:43–53, Oaknin-Bendahan et al, Neuroreport 1995 27;6:785–8, Nordio et al Proc Soc Exp Biol Med 1989; 191:321–5, Zisapel et al, Eur J Pharmacol 1987: 136, 259–60). To the best of the present inventors' knowledge, it has never been previously suggested that other N-(2,4-dinitrophenyl)-5-methoxytryptamines, or their ether or thioether analogs, might have potential use for interacting with the melatoninergic system.

The entire contents of the above-cited patents, patent applications and literature articles are deemed to be incorporated herein by reference.

SUMMARY OF THE INVENTION

In one aspect, the present provides compounds having the formula (I):

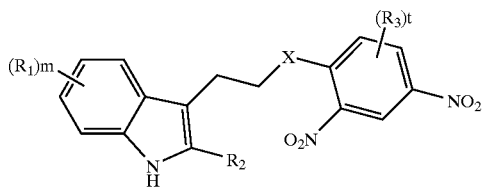

and their acid addition salts where the compounds are basic, wherein:

each of $R_1$, $R_2$ and $R_3$ is independently selected from among hydrogen, halogen, $C_{1-4}$ alkyl, $C_{1-4}$ alkoxy, NR'R", N(R')C(:O)R°, nitro, aryl, aryl-$C_{1-4}$ alkyl, or aryl-$C_{1-4}$ alkoxy, R° is $C_{1-4}$ alkyl or aryl, and each of R' and R" is independently H or $C_{1-4}$ alkyl, or R'=R"=ClCH$_2$CH$_2$, or NR'R" constitutes a saturated heterocyclic ring containing 3–8 ring members; m is 0–4; t is 0–3; X is NH, N—$C_{1-4}$ alkyl, O or S; provided that X is not NH when simultaneously $(R_1)_m$ is 5-methoxy, $R_2$ is H or I and t=0.

In the above definition, "aryl" is the monovalent residue of an unsubstituted or substituted aromatic nucleus, preferably a benzene ring, but it may also be e.g., another monovalent carbocyclic aryl residue such as naphthyl, or the monovalent residue of a heterocyclic aromatic ring such as furan, thiophene, pyrrole, pyridine, benzopyran or benzothiophene. When aryl is substituted, the substituent may be, e.g., one or more of hydroxy, $C_{1-4}$-alkoxy, halogen, cyano, nitro, carboxylic acid, ester or amide, sulfonic acid, ester or amide, sulfone, sulfoxide or halogenated $C_{1-4}$-alkyl such as chloro- or dichloro-methyl or CF$_3$, amino, mono ($C_{1-4}$-alkyl)amino, di($C_{1-4}$-alkyl)amino, or $C_{1-4}$-alkyl.

In another aspect, the invention provides a pharmaceutical formulation which comprises at least one pharmaceutically acceptable diluent, preservative, solubilizer, emulsifier, adjuvant, and/or carrier, and at least one member of the group consisting of the compounds of the invention as defined above and pharmaceutically acceptable salts thereof.

In yet another aspect, the invention provides use of at least one member of the group consisting of the compounds of the invention as defined above and pharmaceutically acceptable salts thereof, in the manufacture of a medicament for interacting with the melatoninergic system, e.g. a medicament for use in animal breeding, or for the prevention or treatment of prostate conditions, impotence, cardiovascular disorders, central nervous system and psychiatric disorders, chronobiological-based disorders endocrine indications, neoplastic conditions, immune system, conditions associated with senescence, ophthalmological diseases, cluster headache and migraine.

In still another aspect, the invention provides a method for treating a medical condition in a mammal (human or non-human) which is susceptible to alleviation by treatment with a medicament which interacts with the melatoninergic system, which comprises treating such condition with an effective amount of at least one member of the group consisting of the compounds defined in claim 1 and pharmaceutically acceptable salts thereof.

DETAILED DESCRIPTION OF THE INVENTION

Without prejudice to the generality of the definition of the compounds of the present invention, presently preferred sub-groups of compounds having the above formula are the following:

those wherein m=0, t=1, $R_3$ is N(R')C(:O)R° in the 3-position of the unfused benzene ring and X is NH, NH—$C_{1-4}$ alkyl or O;

those wherein m=1, t=1, $R_1$ is methyl or methoxy in the 5-position of the indole ring, $R_3$ is N(R')C(:O)R° in the 3-position of the unfused benzene ring and X is NH, NH—$C_{1-4}$ alkyl or O;

those wherein m=0, t=1, $R_3$ is NH$_2$ in the 3-position of the unfused benzene ring and X is NH, NH—$C_{1-4}$ alkyl or O;

those wherein m=1, t=1, $R_1$ is methyl or methoxy in the 5-position of the indole ring, $R_3$ is NH$_2$ in the 3-position of the unfused benzene ring and X is NH, NH—$C_{1-4}$ alkyl or O;

those wherein m=0 or 1, t=0, and when m=-1, $R_1$ is methyl in the 5-position of the indole ring.

The pharmaceutical formulation according to the invention is preferably characterized by at least one of the following features:

(i) it is adapted for oral, rectal, parenteral, transbuccal, intrapulmonary (e.g. by inhalation) or transdermal administration;

(ii) it is in unit dosage form, each unit dosage comprising an amount of said at least one member which lies within the range of 0.0025–1000 mg;

(iii) it is a controlled release formulation, wherein said at least one member is released at a predetermined controlled rate.

In the pharmaceutical formulations of the present invention, the pharmaceutically acceptable diluents, preservatives, solubilizers, emulsifiers, adjuvants and carriers are those conventionally used in pharmaceutical and veterinary formulations. The present pharmaceutical formulations may be adapted for administration to humans and/or animals.

For oral administration, the pharmaceutical formulations may be utilized as e.g. tablets, capsules, emulsions, solutions, syrups or suspensions. For parenteral administration, the formulations may be utilized as ampoules, or otherwise as suspensions, solutions or emulsions in aqueous or oily vehicles. The need for suspending, stabilizing and/or dispersing agents will of course take account of the fact of the solubility or otherwise of the active compounds, in the vehicles which are used in particular embodiments. The formulations may additionally contain e.g. physiologically compatible preservatives and antioxidants.

The pharmaceutical formulations may also be utilized as suppositories with conventional suppository bases such as cocoa butter or other glycerides. Alternatively, the formulations may be made available in a depot form which will release the active composition slowly in the body, over a preselected time period.

The compounds of the invention may further be administered by using transbuccal, intrapulmonary or transdermal delivery systems.

By way of further elaboration or explanation of conditions which it is presently contemplated may be amenable to treatment by administration of the present compounds, such conditions include benign and tumor prostate growth, and impotence; cardiovascular disorders including hypertension, preventing blood coagulation and protection from ischemic strokes; central nervous system and psychiatric disorders, e.g., sleep disorders, epilepsy and other convulsive disorders, anxiety, psychiatric diseases, neuropathy, neuro-degenerative diseases e.g. Alzheimer's, Parkinson's and Huntigton's diseases, fever and analgesia; chronobiological-based disorders, e.g., jet lag, circadian sleep disorders such as delayed sleep syndrome, shift-work problems, and seasonal-related disorders e.g. seasonal affective disorder (SAD); endocrine indications, e.g., contraception and infertility, precocious puberty, premenstrual syndrome, hyperprolactinemia, and growth hormone deficiency; neoplastic diseases including e.g. cancer and other proliferative diseases; immune system disorders including AIDS; conditions associated with senescence; ophthalmological diseases; cluster headache, migraine; Tardive dyskinesia, diabetes stabilization and weight gain disorders (leptin, obesity), and as an aid to animal breeding, e.g., regulation of fertility, puberty, pelage color.

It is still further contemplated that the present compounds (and particularly those where in formula (I) having antioxidant and radical scavenging activity and the invention thus includes skin-protective and cosmetic compositions for topical application, such as (merely by way of illustrative examples) ointments, creams, salves and lotions, which comprise at least one compound according to the present invention, together with at least one diluent, carrier and adjuvant The invention will be illustrated by the following Examples.

EXAMPLE 1

N-(2,4-dinitrophenyl)tryptamine (ML-25)

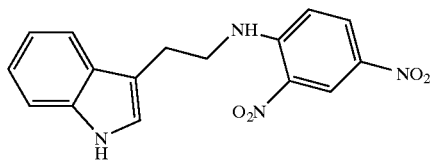

1 mMole of tryptamine was dissolved in 100 ml of water and the pH was adjusted to pH 8.3 with 2.5 moles of sodium bicarbonate (NaHCO$_3$), A 1.5% solution of 2,4-dinitrofluorobenzene in 200 liters ethanol was added and the mixture was stirred during 2 hours at room temperature. The desired product precipitates out, it is washed and dried. The product is obtained in 90% yield, and TLC (chloroform, silica-gel plates, reveals one yellow spot (Rf=0.84) which is well resolved from the starting materials under the same conditions.

EXAMPLE 2

N-(2,4-dinitrophenyl)-5-methyltryptamine (ML-28)

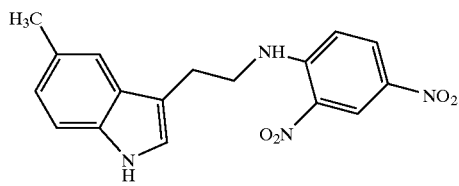

1 mMole of 5-metyltryptamine was dissolved in 100 ml of water and the pH was adjusted to pH 8.3 with 2.5 moles of sodium bicarbonate (NaHCO$_3$), A 1.5% solution of 2,4-dinitrofluorobenzene in 200 ml ethanol was added and the mixture was stirred during 2 hours at room temperature. The desired product precipitates out, it is washed and dried. The product is obtained in 85% yield, and TLC (chloroform, silica-gel plates, reveals one yellow spot (Rf=0.8) which is well resolved from the starting materials under the same conditions.

EXAMPLE 3

2,4-dinitro-5-tryptylaminoacetanilide (ML-26)

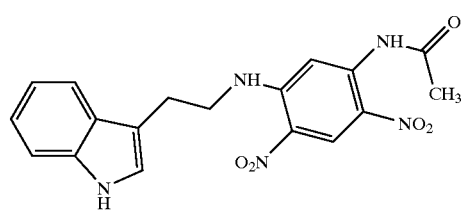

1 mMole of tryptamine was dissolved in 100 ml of water and the pH was adjusted to pH 8.3 with 2.5 moles of sodium bicarbonate (NaHCO$_3$), A 1.5% solution of 2,4-dinitro-5-fluoroacetanilide in 200 ml ethanol was added and the mixture was stirred during 2 hours at room temperature. The desired product precipitates out, it is washed and dried. The product is obtained in 80% yield, and TLC (chloroform, silica-gel plates, reveals one yellow spot (Rf=0.76) which is well resolved from the starting materials under the same conditions.

EXAMPLE 4

2,4-dinitro-5-(5'-methyltryptyl)aminoacetanilide (ML-29)

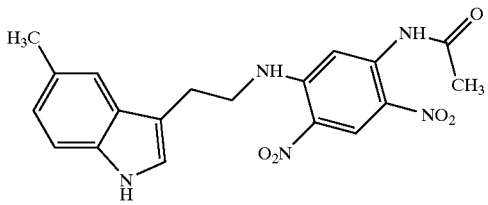

1 mMole of 5-methyltryptamine was dissolved in 100 ml of water and the pH was adjusted to pH 8.3 with 2.5 moles of sodium bicarbonate (NaHCO$_3$), A 1.5% solution of 2,4-dinitro-5-fluoroacetanilide in 200 ml ethanol was added and the mixture was stirred during 2 hours at room temperature. The desired product precipitates out, it is washed and dried. The product is obtained in 95% yield, and TLC (chloroform, silica-gel plates, reveals one yellow spot (Rf=0.7) which is well resolved from the starting materials under the same conditions.

EXAMPLE 5

2,4-dinitro-5-(5'-methoxytryptyl)aminoacetanilide (ML-30)

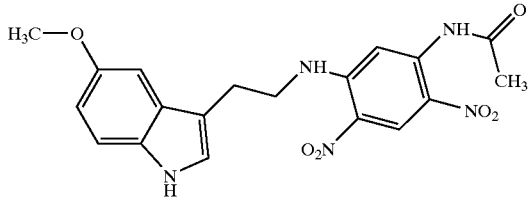

1 mMole of 5-methoxytryptamine was dissolved in 100 ml of water and the pH was adjusted to pH 8.3 with 2.5 moles of sodium bicarbonate (NaHCO$_3$), A 1.5% solution of 2,4-dinitro-5-fluoroacetanilide in 200 ml ethanol was added and the mixture was stirred during 2 hours at room temperature. The desired product precipitates out, it is washed and dried. The product is obtained in 85% yield, and TLC (chloroform, silica-gel plates, reveals one yellow spot (Rf=0.57) which is well resolved from the starting materials under the same conditions.

EXAMPLE 6

N-(2,4-dinitro-5-aminophenyl)tryptamine (ML-27)

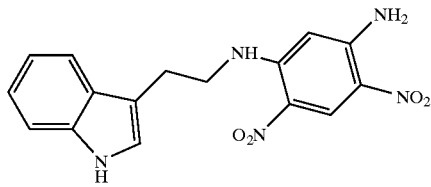

1 mMole of tryptamine was dissolved in 100 ml of water and the pH was adjusted to pH 8.3 with 2.5 moles of sodium bicarbonate (NaHCO$_3$), A 1.5% solution of 2,4-dinitro-5-fluoroaniline in 200 ml ethanol was added and the mixture was stirred during 2 hours at room temperature. The desired product precipitates out, it is washed and dried. The product is obtained in 90% yield, and TLC (chloroform, silica-gel plates, reveals one yellow spot (Rf=0.57) which is well resolved from the starting materials under the same conditions

EXAMPLE 7

N-(2,4-dinitro-5-aminophenyl)-5'-methyltryptamine (ML-31)

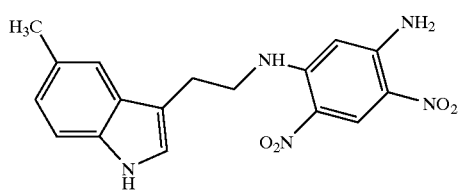

1 Mole of 5-methyltryptamine was dissolved in 100 ml of water and the pH was adjusted to pH 8.3 with 2.5 moles of sodium bicarbonate (NaHCO$_3$), A 1.5% solution of 2,4-dinitro-5-fluoroaniline in 200 ml ethanol was added and the mixture was stirred during 2 hours at room temperature. The desired product precipitates out, it is washed and dried. The product is obtained in 90% yield, and TLC (chloroform, silica-gel plates, reveals one yellow spot (Rf=0.59) which is well resolved from the starting materials under the same conditions.

EXAMPLE 8

N-(2,4-dinitro-5-aminophenyl)-5'-methoxytryptamine (ML-32)

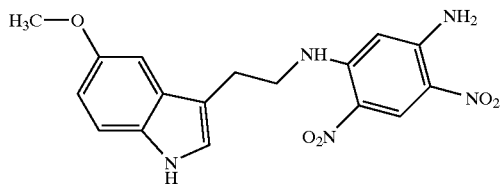

1 mMole of 5-methoxytryptamine was dissolved in 100 ml of water and the pH was adjusted to pH 8.3 with 2.5 moles of sodium bicarbonate (NaHCO$_3$), A 1.5% solution of 2,4-dinitro-5-fluoroaniline in 200 ml ethanol was added and the mixture was stirred during 2 hours at room temperature. The desired product precipitates out, it is washed and dried. The product is obtained in 95% yield, and TLC (chloroform, silica-gel plates, reveals one yellow spot (Rf=0.57) which is well resolved from the starting materials under the same conditions.

EXAMPLE 9

O-2,4-dinitrophenyl-5'-methoxytryptophol (ML-33)

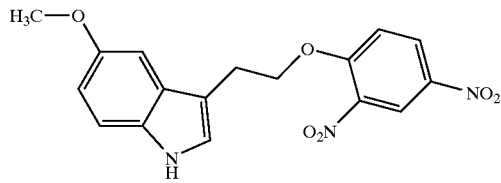

To a solution of 5-methoxytryptophol 1 (700 mg, 3.7 mmol) in 3 ml of dichloromethane (DCM) was added dropwise a solution of 2,4-dinitro-5-fluoro benzene (205 mg, 4.0 mmol) in DCM, and the mixture was stirred under argon. Triethylamine (410 mg, 4.1 mmol) was added slowly and the mixture was stirred overnight, after which the solvent was evaporated, and TLC (chloroform, silica-gel plates, reveals one yellow spot (Rf=0.80) which is well resolved from the starting materials under the same conditions. The crude product was dissolved in chloroform (200 ml) and washed with 0.1 N HCl (2×200 ml), with 1 N NaOH (2×200 ml) and 1 with water (200 ml). The organic layer was dried with $MgSO_4$ and concentrated in vacuo. Flash chromatography on silica gel, with chloroform as eluent, resulted in pure 5-methoxytryptophyl 2,4-dinitrophenyl ether (890 mg, 2.5 mmol, 67% yield) as a bright yellow powder.

Biological Testing of Compounds of the Invention

Experiment 1

Table 1: Effects of ML Compounds of the Invention on Glutamate-induced Oxidative Toxicity in Hippocampal Cell Line (HT22)

The changes in the mithochondrial membrane potential was assessed using the fluorescent probe 5,5',6,6'-tetrachloro-1,1',3,3'-tetraethylbenzimidazolcarbocyanine iodide (JC-1) according to Nuydens et al, 1999, L of Neuroscience; 92, 153–9. Immortalized mouse hipocampal cells (HT-22) were maintained in Dulbecco's modified minimal essential medium (DMEM) supplemented with 10% fetal bovine serum and passaged by trypsinization. Cells (3000 per 96 palte well) were cultured for 24h with DMEM containing 5 mM glutamate and were treated with $10^{-7}$ M of the ML compounds. Cells were then loaded with JC-1 by changing the culture medium to Phosphate buffered saline (PBS) containing 1 g/L glucose and 10 uM JC-1 for 10 mln. at 37° and were washed once. Flouresence was then measured in a plate reader at excitation/emission wavelengths of 480/530 nm and 530/590 nm. The ratio of the fluoresence intensities in the two wavelengths 530/590:480/530 is an indication of the mitochondrial membrane potential. Decrease in this ratio indicates depolarization of the mitochondrial membrane due to damage induced by anoxic or other phathological situations leading to apoptosis of cells. The results (table 1) demonstrate the decreased fluorescence ratio by glutamate indicating damage to mitochondrial membrane potential in the hippocampal cells. Melatonin, ML-23 and four compounds of the invention (ML-25, ML-27, ML-26, ML-30) significantly protected against glutamate-mediated damage to the mitochondria so that the fluorescence ratio remained high compared to cells treated with glutamate. Among these, three (ML-23, ML-25, ML-26) did not decrease membrane potential of the control cells whereas others (ML-27 and ML-30) decreased it. Other compounds in the group presented in Table 1 (ML-29, ML-32, ML-31) decreased mitochondrial membrane potential in control cells without providing protection against glutamate and one (ML-28) elevated the potential in control cells but did not protect against glutamate induced damage.

This experiment indicates a direct inhibitory action of compounds of the invention on mitochondrial membrane potential, which resemble the effect of melatonin.

TABLE 1

| control conditions | | +glutamate 5 mM | | |
|---|---|---|---|---|
| | JC-1 ratio A | | JC-1 ratio B | JC-1 ratio B/A (%) |
| Control | 2.46 | Control | 2.09 | 85 |
| Melatonin | 2.48 | Melatonin | 2.44 | 98 |
| ML-23 | 2.19 | ML-23 | 1.97 | 90 |
| ML-25 | 2.21 | ML-25 | 2.01 | 91 |
| ML-26 | 2.16 | MI-26 | 2.11 | 98 |
| ML-27 | 1.80 | MI-27 | 1.83 | 102 |
| ML-28 | 2.77 | ML-28 | 2.28 | 82 |
| ML-29 | 2.28 | ML-29 | 1.79 | 78 |
| ML-30 | 1.83 | ML-30 | 2.13 | 116 |
| ML-31 | 1.93 | ML-31 | 1.57 | 81 |
| ML-32 | 2.15 | ML-32 | 1.76 | 82 |

Experiment 2
$^{125}$I-Melatonin Binding in Membranes of Hamster Brain 2 whole hamster brains were homogenized with Teflon-glass homogenizer in 10 vol/g tissue of ice cold Tris-HCl buffer (50 mmol/L Tris, 5 mmol/L CaCl2, pH=7.4) and spun at 10,000 g for 10 min. the supernatant were spun at 100,000 g for two hours to yield a crude synaptosomal pellet (P2). Aliquots of suspended P2 (20 ul) were incubated at 37° C. with $^{125}$I-melatonin (250 pM) for 60 mln. in Tris-Hcl buffer in the absence or presence of 1 nM-100 $\mu$M test-substances (ML compounds and melatonin). The binding reaction was terminated by the addition of 4 ml ice cold Tris buffer. Membranes were then collected by vacuum filtration using GF/C glass fiber filters and washed with 3×4 ml ice-cold buffer. The filters containing the bound $^{125}$I-melatonin were assayed for the amount of radioactivity in a γ counter. The results (table 2) demonstrate the competition of ML compounds on specific $^{125}$I-melatonin binding to membrane fraction of rat brain. ML-29, ML-30 and ML-31 ($10^{-6}$M) inhibited ($\geq$20%) the specific $^{125}$I-melatonin binding. ML-27, ML-28 and ML-23 reduced the specific $^{125}$I-melatonin binding to a lesser extent (~13%). Melatonin ($10^{-6}$M) also decreased the specific $^{125}$I-melatonin binding to a similar extent (20%).

TABLE 2

| Competitor concentration: | 0 | 10-6M | % bound | 10-7M | % bound |
|---|---|---|---|---|---|
| Melatonin | 424 | 335 | 79 | 377 | 89 |
| ML-23 | 463 | 403 | 87 | 435 | 94 |
| ML-25 | 429 | 390 | 91 | 396 | 92 |
| ML-26 | 417 | 411 | 99 | 435 | 104 |
| ML-27 | 486 | 426 | 87 | 448 | 92 |
| ML-28 | 418 | 365 | 87 | 381 | 91 |
| ML-29 | 447 | 358 | 80 | 404 | 90 |
| ML-30 | 509 | 409 | 80 | 488 | 96 |
| ML-31 | 464 | 334 | 72 | 438 | 94 |
| ML-32 | 452 | 419 | 93 | 408 | 90 |

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims.

What is claimed is:

1. A compound having the formula (I):

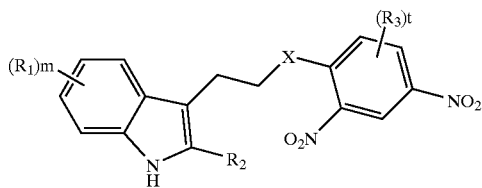

and their acid addition salts where the compounds are basic, wherein:

each of $R_1$, and each of $R_2$ and $R_3$ is independently selected from among hydrogen, halogen, $C_{1-4}$ alkyl, $C_{1-4}$ alkoxy, NR'R", N(R')C(:O)R°, nitro, aryl, aryl-$C_{1-4}$ alkyl, or aryl-$C_{1-4}$ alkoxy, R° is $C_{1-4}$ alkyl or aryl, and each of R' and R" is independently H or $C_{1-4}$ alkyl, or R'=R"=ClCH$_2$CH$_2$, or NR'R" constitutes a saturated heterocyclic ring containing 3–8 ring members; m is 0–4; t is 0–3; and X is NH, N—$C_{1-4}$ alkyl, O or S; provided that X is not NH when simultaneously $(R_1)_m$ is 5-methoxy, $R_2$ is H or I and t=0, and that X is not S when simultaneously $R_2$ is H and m=t=0.

2. A compound according to claim 1, wherein m=0, t=1, $R_3$ is N(R')C(:O)R° in the 3-position of the unfused benzene ring and X is NH, NH—$C_{1-4}$ alkyl or O.

3. A compound according to claim 1, wherein m=1, t=1, $R_1$ is methyl or methoxy in the 5-position of the indole ring, $R_3$ is N(R')C(:O)R° in the 3-position of the unfused benzene ring and X is NH, NH—$C_{1-4}$ alkyl or O.

4. A compound according to claim 1, wherein m=0, t=1, $R_3$ is NH$_2$ in the 3-position of the unfused benzene ring and X is NH, NH—$C_{1-4}$ alkyl or O.

5. A compound according to claim 1, wherein m=1, t=1, $R_1$ is methyl or methoxy in the 5-position of the indole ring, $R_3$ is NH$_2$ in the 3-position of the unfused benzene ring and X is NH, NH—$C_{1-4}$ alkyl or O.

6. A compound according to claim 1, wherein m=0 or 1, t=0, and when m=1, $R_1$ is methyl in the 5-position of the indole ring.

7. A compound according to claim 1, which is selected from the following:

N-(2,4-dinitrophenyl)tryptamine
N-(2,4-dinitrophenyl)-5-methyltryptamine
2,4-dinitro-5-tryptylaminoacetanilide
2,4-dinitro-5-(5'-methyltryptyl)aminoacetanilide
2,4-dinitro-5-(5'-methoxytryptyl)aminoacetanilide
N-(2,4-dinitro-5-aminophenyl)tryptamine
N-(2,4-dinitro-5-aminophenyl)-5'-methyltryptamine
N-(2,4-dinitro-5-aminophenyl)-5'-methoxytryptamine
O-2,4-dinitrophenyl-5'-methoxytryptophol.

8. A pharmaceutical formulation, for at least one use selected from animal breeding, for the prevention or treatment of prostate conditions, impotence, cardiovascular disorders, central nervous system and psychiatric disorders, chronobiological-based disorders endocrine indications, neoplastic conditions, immune system disorders, conditions associated with senescence, ophthalmological diseases, or cluster headache and migraine, which comprises at least one pharmaceutically acceptable diluent, preservative, solubilizer, emulsifier, adjuvant, and/or carrier, and at least one member of the group consisting of the compounds having formula (I) as depicted in claim 1 and pharmaceutically acceptable salts thereof, wherein: each of $R_1$, and each of $R_2$ and $R_3$ is independently selected from among hydrogen, halogen, $C_{1-14}$ alkyl, $C_{1-4}$ alkoxy, NR'R", N(R')C(:O)R°, nitro, aryl, aryl-$C_{1-4}$ alkyl, or aryl-$C_{1-4}$ alkoxy, R° is $C_{1-4}$ alkyl or aryl, and each of R' and R" is independently H or $C_{1-4}$ alkyl, or R'=R"=ClCH$_2$CH$_2$, or NR'R" constitutes a saturated heterocyclic ring containing 3–8 ring members; m is 0–4; t is 0–3; and X is NH, N—$C_{1-4}$ alkyl, O or S; provided that X is not NH when simultaneously $(R_1)_m$ is 5-methoxy, $R_2$ is H or I and t=0.

9. A pharmaceutical formulation according to claim 8, which is characterized by at least one of the following features:

(i) it is adapted for oral, rectal, parenteral, transbuccal, intrapulmonary or transdermal administration;

(ii) it is in unit dosage form, each unit dosage comprising an amount of said at least one member which lies within the range of 0.0025–1000 mg;

(iii) it is a controlled release formulation, wherein said at least one member is released at a predetermined controlled rate.

10. A composition selected from skin-protective and cosmetic compositions for topical application, which comprises at least one compound of formula (I) as defined in claim 8 having activity selected from antioxidant and radical scavenging activity, together with at least one diluent, carrier and adjuvant.

* * * * *

UNITED STATES PATENT AND TRADEMARK OFFICE
CERTIFICATE OF CORRECTION

PATENT NO. : 6,780,884 B2
DATED : August 24, 2004
INVENTOR(S) : Zisapel et al.

It is certified that error appears in the above-identified patent and that said Letters Patent is hereby corrected as shown below:

<u>Title page, Item [54] and Column 1, line 1</u>,
Title, delete "DERIVATING" and insert therefore -- DERIVATIVES --.

Signed and Sealed this

Fourteenth Day of December, 2004

JON W. DUDAS
*Director of the United States Patent and Trademark Office*